United States Patent [19]

Schütz et al.

[11] Patent Number: 5,612,058
[45] Date of Patent: Mar. 18, 1997

[54] LYOPHILIZED EMULSION CONTAINING AN ACTIVE SUBSTANCE

[75] Inventors: Andreas Schütz, Cologne; Hans-Jürgen Mika, Bonn; Frank Sievert, Burscheid; Bernhard Emschermann, Düsseldorf, all of Germany

[73] Assignee: Schwarz Pharma AG, Germany

[21] Appl. No.: 491,862

[22] PCT Filed: Dec. 10, 1993

[86] PCT No.: PCT/DE93/01188

§ 371 Date: Jun. 23, 1995

§ 102(e) Date: Jun. 23, 1995

[87] PCT Pub. No.: WO94/13394

PCT Pub. Date: Jun. 23, 1994

[30] Foreign Application Priority Data

Dec. 24, 1992 [DE] Germany .............. 42 44 122.6

[51] Int. Cl.⁶ ........................................... A61K 9/14
[52] U.S. Cl. ..................... 424/489; 424/488; 424/455
[58] Field of Search ................. 424/450, 489, 424/488, 490, 455, 493; 264/46

[56] References Cited

U.S. PATENT DOCUMENTS 5,192,549  3/1993  Barenolz et al. .................. 424/450
5,407,609  4/1995  Tice et al. ........................... 264/46

FOREIGN PATENT DOCUMENTS 0159237  10/1985  European Pat. Off. .
0211257  9/1986  European Pat. Off. .
9217162  10/1992  WIPO .

OTHER PUBLICATIONS

Japan Abstract Freeze Dried oil-in-water Emulsion Prepn. #J60239417-A Nov. 28, 1985 (8603).
PCT International Search Report for PCT/DE 93/01188.

*Primary Examiner*—Thurman K. Page
*Assistant Examiner*—W. Benston
*Attorney, Agent, or Firm*—Merchant, Gould, Smith, Edell, Welter & Schmidt

[57] ABSTRACT

The invention relates to a lyophilized emulsion composition which contains an active substance and which can be redispersed with water to give the original emulsion, and to a process for the preparation thereof.

The redispersed emulsion is suitable for parenteral use.

18 Claims, No Drawings

LYOPHILIZED EMULSION CONTAINING AN ACTIVE SUBSTANCE

The present invention relates to a lyophilized emulsion which can be redispersed with water to give the original emulsion.

In particular, the invention relates to a fat emulsion which contains an active substance and whose external aqueous phase has been removed by freeze-drying and which can be redispersed by addition of water spontaneously to give the original emulsion with a particle size distribution corresponding to the initial formulation.

Emulsions are disperse systems composed of two mutually immiscible liquids, one of which, the internal, disperse phase, is finely dispersed in the other, the external, continuous phase.

Fat emulsions are emulsion systems in which the internal, disperse phase consists of very fine fat particles which are homogeneously dispersed in the external phase which is composed of water. Emulsion formulations of this type are preferably used parenterally and are particularly used for intravenous nutrition of patients unable to take food by mouth.

Fat emulsions which can be administered intravenously make high demands on the tolerability of their ingredients and the particle size of the fat particles. Preferably used as fat component are oils with a high content of unsaturated fatty acids such as soya bean, safflower and cottonseed oils, as emulsifiers are lecithins such as egg, soya and cerebral lecithins, as well as antioxidants such as tocopherol acetate and other auxiliary substances.

The fat particles should, in order to avoid changes in blood pressure and the risk of embolism, not exceed an average particle size of 1 µm.

The emulsion is normally prepared by preemulsifying the heated oil and aqueous phases with a mixer, followed by microfine emulsification using a high-pressure homogenizer and subsequent sterilization with superheated steam.

The "Handbook on Injectable Drugs" (American Society of Hospital Pharmacists, pages 237–244 (1986), Lawrence A. Trissel) describes some commercially available formulations. They contain soya bean oil or safflower oil, egg lecithin, glycerol and water and have average particle sizes of $\leq 0.5$ µm.

Fat emulsions are also repeatedly used as vehicle systems for lipophilic medicinal substances to be administered parenterally. The aim in this case is to increase the therapeutic efficacy and safety of medicinal substances by controlled release from emulsion systems.

In accordance with their solubility properties, lipophilic active substances in emulsions are partly or completely incorporated in the fat particles. This means that their pharmacokinetic behaviour is crucially determined by the pharmacokinetic behaviour of the vehicle formulations from which the active substance is first released. Delayed release avoids high local concentrations of active substance, reduces degradation and thus increases the duration of action.

Emulsion systems of this type are particularly advantageous for prostaglandins, especially prostaglandin $E_1$ ($PGE_1$). $PGE_1$ is a highly active tissue hormone which is successfully used, for example, for the treatment of arterial occlusive disease. Used for this purpose is a $PGE_1$-α-cyclodextrin complex which, dissolved in physiological saline solution, is infused parenterally, preferably intraarterially, as close as possible to the body region to be treated. However, high pressure conditions and small dilution effects during the intraarterial infusion make high demands on the equipment and the training of the treating physician. Although intravenous infusion is simpler to perform by comparison, even in this case infusion is possible only slowly and in relatively high dilution because of the local irritant effect of $PGE_1$. Overall, the extended residence time of the active substance in the vascular system before reaching the target site and, in particular, the additional passage through the pulmonary circulation leads to increased degradation of active substance. Both intra-arterial and intravenous infusions make high demands on the equipment and careful adjustment of the infusion rate and are therefore usually performed in hospital and not by the established physician, which impedes wide use of the valuable active substance in the therapy of arterial occlusive disease.

These problems can be avoided by incorporating $PGE_1$ in a fat emulsion. Delayed release of active substance avoids high local concentrations, reduces degradation of active substance and increases the duration of action so that formulations of this type are also suitable for intravenous bolus injection.

The process for preparing such fat emulsions containing active substances substantially corresponds to the above-mentioned preparation of a fat emulsion, with the difference that the active substance to be incorporated is dissolved in the oil phase before carrying out the preemulsification. Although $PGE_1$-containing fat emulsions of this type are suitable for solving the disadvantages described for the conventional use of $PGE_1$, they have low storage stability owing to hydrolytic degradation of the active substance, which impedes their general utilizability.

One possibility for stabilizing the active substance within the emulsion comprises removal of the substances destabilizing the active substance. One example of this is given in U.S. Pat. No. 4,684,633 which describes the stabilization of active substances brought about by using phosphatidylethanolamine-free egg lecithin in an emulsion composition containing prostaglandin, soya oil, egg lecithin, glycerol and water. However, stabilization of active substances is shown only for the condition of brief sterilization at 125° C. for 2.2 min. There are no data on the stability on long-term storage. The formulation also contains water so that degradation of active substance as a result of hydrolysis cannot in principle be ruled out. A fundamental disadvantage is that the stabilization occurs only to the stated active substances and is not generally applicable.

Besides stabilization of the active substance in a fat emulsion ready for administration, fat emulsions with intact active substance can also be used by being prepared only immediately before use. One example of this is given by EP 0 331 755. It describes a kit consisting of a conventional fat emulsion and either an active substance solution in water, liquid polyalkylene glycols, liquid alkylethanolamines or liquid alcohols containing a plurality of hydroxyl groups, or an active substance composition consisting of active substance, saccharides and/or amino acids, which are combined and vigorously mixed immediately before use. Vigorous mixing is absolutely necessary to make it possible to disperse the active substance in the fat emulsion. Thus, for example, the active substance emulsion described in Example 5 is prepared by mixing for 2–3 minutes. However, long mixing times are disadvantageous on use.

An example relating to prostaglandins which is mentioned in EP 0 331 755, Example 3, describes an active substance composition consisting of a prostaglandin and triethanolamine. However, triethanolamine is not without objections physiologically so that its use in pharmaceutical formulations, especially in injectable products, should be avoided where possible.

There has thus been a continuing need for an emulsion formulation which avoids PGE₁ degradation as a consequence of hydrolysis, is physiologically unobjectionable and is simple to handle. A formulation of this type ought to preclude in principle hydrolytic degradation of active substance on storage due to absence of water, be easily redispersible by addition of water, and ensure dispersion of the active substance in the fat phase of the emulsion from the outset.

A formulation of this type is to be prepared by lyophilization of a fat emulsion containing active substance, which as anhydrous formulation leads to the expectation of storage stability and can be reconstituted with water to give the original formulation before administration. However, investigations show that lyophilization of emulsions lead to coalescence of the fat particles and thus to enlargement of the particles thereof or even to their complete destruction. Various research groups have repeatedly attempted to prevent this coalescence of emulsions as a consequence of lyophilization by adding cryoprotection agents. However, their results show that even this measure is unable to prevent an increase in the average particle diameter [Lladser, M. et al.: The use of supports in the lyophilization of oil-in-water emulsions, J. Pharm. Pharmacol 20, 450–455 (1968); Rambhan, D. et al.: Stability Studies on Lyophilized O/W Emulsions, Indian J. Pharm. 39, 52–55 (1977)]. Bensouda et al. further show that the increase in the average particle diameter as a consequence of lyophilization increases with decreasing size of the emulsion particles [Bensouda, Y. et al.: Freeze-drying of Emulsions—Influence of Congealing on Granulometry Research of a Cryoprotection Agent, Pharm. Acta Helv. 64, 40–44 (1989)]. However, emulsions for intravenous administration should, in order to avoid embolism, have an average particle size less than or equal to 1 μm. Prevention of an increase in particle size as a consequence of lyophilization therefore appears to be particularly difficult, but is indispensible for safety reasons.

Lyophilized reconstitutable emulsions which are said also to be suitable for intravenous use are described in the documents JP 60239417 and ZA 86 04 032. JP 60239417 describes the preparation of lyophilized emulsion systems with the addition of cryoprotection agents such as saccharides and sugar alcohols and water-soluble polymers such as polyvinylpyrrolidone, gelatin and hydroxypropylcellulose. However, it is evident from the examples that the particle diameters of the redispersed emulsions are all higher than in the initial emulsion. ZA 86 04 032 discloses lyophilized emulsion compositions and a method for their preparation. After preparation of a conventional fat emulsion by known processes and addition of a bulking sugar, the emulsion is sprayed into a boiling liquid with a boiling point below –20° C. and subsequently lyophilized. The examples show, however, that even in this case the average particle diameter of the fat particles after reconstitution with water is higher than in the initial emulsion.

Lyophilized emulsions which have, after reconstitution with water, a particle dispersion corresponding to the initial formulation are not present in the prior art.

Surprisingly, an anhydrous emulsion composition which contains active substance and which contains at least one cryoprotection agent/bulking agent and can be redispersed by addition of water to give the original, water-containing, active-substance containing emulsion with corresponding particle size distribution has now been found. An emulsion composition having no coherent external aqueous phase is termed anhydrous. A composition of this type avoids hydrolytic degradation of the active substance(s) and shows high storage stability.

The emulsion composition advantageously contains hydrophilic emulsifiers and acetylated monoglycerides. Hydrophilic emulsifiers are surfactants whose emulsifying behaviour is crucially determined by their hydrophilic groups and preferably form fat-in-water emulsions.

The emulsion composition preferably contains ethoxylated triglycerides or polyoxyethylene hydroxy fatty acid esters and acetylated monoglycerides with unsaturated double bonds.

The emulsion composition particularly contains glycerol polyethylene glycol ricinoleate (macrogol glycerol ricinoleate) or polyoxyethylene 660 12-hydroxystearate (macrogol 660 12-hydroxystearate) and diacetylated monoglycerides or a mixture of diacetylated and partially acetylated monoglycerides.

Particularly advantageous in this case are acetylated monoglycerides which contain 2% by weight to 40% by weight, preferably 20% by weight, of partially acetylated monoglycerides.

According to an expedient embodiment of the present invention, the hydrophilic emulsifiers and the acetylated monoglycerides are present in a ratio of 1:10 to 2:1 by weight, preferably in a ratio of 2:3 by weight.

According to a particularly preferred embodiment of the anhydrous emulsion composition according to the invention, the latter contains at least one active substance from the active substance group of prostaglandins, especially PGE₁.

Another advantageous embodiment of the emulsion composition according to the invention contains as cryoprotection agent/bulking agent physiologically tolerated mono-, di- or oligosaccharides, especially lactose or sugar alcohols such as sorbitol and/or mannitol.

According to another preferred embodiment of the emulsion composition according to the invention, the latter contains at least one customary antioxidant, advantageously from the group of tocopherols such as α-, β-, γ- or δ-tocopherol, preferably α-tocopherol, and the physiologically tolerated salts thereof, such as phosphates, succinates and acetates and/or physiologically tolerated buffer salts.

According to another preferred embodiment of the emulsion composition according to the invention, its internal disperse phase has, after reconstitution with water, average particle diameters of 0.1 μm to 5 μm, preferably 0.2 μm to 1.0 μm.

Another particularly preferred embodiment of the anhydrous emulsion composition according to the invention contains cryoprotection agents/bulking agents and can be redispersed by addition of water to give the original water-containing emulsion with identical particle size distribution.

The emulsion composition according to the invention can be prepared by removing the aqueous phase by lyophilization from an emulsion which has been prepared by the processes and technologies customary in the production of pharmaceuticals.

The invention therefore also relates to a process for the preparation of the active-substance containing anhydrous emulsion composition, according to the invention, which is characterized in that an active-substance containing emulsion is prepared in a conventional way and its external aqueous phase is subsequently removed by freeze-drying.

It is possible to incorporate in the emulsion composition according to the invention hydrophilic active substances by dissolving in the aqueous phase, and lipophilic active substances by dissolving in the phase containing emulsifier and fat. Alternatively, the active substance can also be added immediately before the lyophilization is carried out, which is particularly advantageous for active substances which are sensitive to hydrolysis and/or unstable to heat. This means that the process for preparing the emulsion composition containing an active substance according to the invention can be adapted in an advantageous manner to suit the physicochemical properties of the active substances. Therefore, in an expedient embodiment of the process according to the invention, at least one active substance is dissolved either in the aqueous phase or in the phase containing emulsifier and fat before emulsification, or at least one active substance is added to the emulsion before it is freeze-dried. Care should be taken in this case that the active substance dispersion within the disperse system is ensured before lyophilization, which can easily be checked by customary methods such as equilibrium dialysis, differential dialysis and ultrafiltration.

Preparation

EXAMPLE 1 emulsion preparation 3.42 g of citric acid monohydrate, 1.57 g of trisodium citrate dihydrate and 60.0 g of lactose were dissolved by heating in 475 g of water for injections. Subsequently, 12.0 g of polyoxyethylene 660 12-hydroxy-stearate and 18.0 g of diacetylated monoglycerides with a hydroxyl number of 25 were dissolved in 30.0 g of absolute ethanol by heating to about 30° C. under an inert atmosphere (nitrogen).

The aqueous phase was transferred into a suitable presterilized reaction vessel (IKALR-A 1000 laboratory reactor, IKA-Werke, Jahnke & Kunkel GmbH, Staufen, Germany) with temperature-control device, stirrer tool and toothed rim disperser (Ultraturrax, IKA-Werke, Jahnke & Kunkel GmbH, Staufen, Germany) and heated to 80° C. while stirring under a vacuum of <1 mbar. While maintaining the vacuum and the stirring, the ethanolic emulsifier lipid phase was slowly injected through a cannula directly into the aqueous phase with simultaneous vigorous homogenization using the Ultraturrax. The mixture was subsequently cooled, with continuous stirring and maintenance of the vacuum, to room temperature while vigorous homogenization was carried out using the toothed rim dispersing rod for about 1 min in several periods. The cooled emulsion was transferred into a presterilized bottle and stored in a refrigerator until processed further.

To incorporate the active substance, 163.9 mg of $PGE_1$-α-cyclodextrin dissolved in 5 ml of water for injections were introduced into a presterilized 500 ml graduated flask and made up to 500 ml with the prepared emulsion, and a sample was taken for particle measurements. The solution containing active substance was transferred under aseptic conditions and using a Dispensette with a capacity of 2 ml/single dose to a height of about 1 cm into presterilized vials. The charged vials were then provided with stoppers, placed in the lyophilizer and frozen at −45° C. for 5 hours. The subsequent lyophilization process was carried out as shown in the following table.

| Time (hours) | Initial temperature (°C.) | Final temperature (°C.) | Pressure (µbar) |
| --- | --- | --- | --- |
| 30 | −40 | −40 | 100 |
| 10 | −40 | 25 | 100 |
| 15 | 25 | 25 | 1 |

Subsequently the vacuum was removed with simultaneous introduction of nitrogen, the vials were closed by hydraulic lowering of the stoppers and were removed from the lyophilizer under aseptic conditions after it had been opened.

They contained cakes which appeared dry and homogeneous and which spontaneously disintegrated on addition of water and formed an emulsion. Example 2

1.5 g of citric acid monohydrate, 2.34 g of trisodium citrate dihydrate and 60 g of lactose were dissolved by heating in 476 g of water for injections. In addition, 12.0 g of glycerol polyethylene glycol ricinoleate and 18.0 g of diacetylated monoglycerides with a hydroxyl number of 4 were dissolved in 30 g of absolute ethanol with gentle heating and under a nitrogen atmosphere. Subsequently, in accordance with the preparation process described in Example 1, the emulsion was prepared, the active substance was incorporated, samples were taken for particle measurement, and lyophilization was carried out.

Likewise as in Example 1, the product cakes which have been formed appeared dry and homogeneous and spontaneously disintegrated to an emulsion on addition of water.

Particle size distribution

To examine the effect of lyophilization and redispersion on the particle size, the volume distributions of the emulsion particles before lyophilization and after freeze-drying and redispersion with water had taken placed were determined by laser light scattering (Malvern Master Sizer, Series 3.01, Malvern Instruments Limited, Spring Lane South, Malvern, Worcestershire, WR14 1AQ, UK). Comparison of the volume distributions reveals even the slightest changes in the particularly critical larger particles because the latter by their nature contribute a larger portion of the total volume. The following table shows the results of measurement of the particle size determination of emulsions prepared according to the invention as in the examples. They contain the maximum particle sizes which characterize the volume distributions and which, together with the smaller particles lying below them in each case, include 10%, 50%, 90% or 99% of the total volume.

| | Maximum size of the particles which, together with the smaller particles in each case, comprise the following volume proportions | | | |
| --- | --- | --- | --- | --- |
| | 10% | 50% | 90% | 99% |
| Example 1 | | | | |
| before lyophilization | 0.20 µm | 0.39 µm | 0.98 µm | 5.07 µm |
| after lyophilization and redispersion with water | 0.19 µm | 0.35 µm | 1.02 µm | 3.32 µm |
| Example 2 | | | | |
| before lyophilization | 0.19 µm | 0.38 µm | 1.09 µm | 4.56 µm |
| after lyophilization and redispersion with water | 0.20 µm | 0.40 µm | 1.17 µm | 4.56 µm |

It is clear that the particle size distributions of the emulsions reconstituted by addition of water agree with the particle size distributions of the initial emulsions.

We claim:

1. An anhydrous emulsion composition comprising at least one active substance, and at least one cryoprotection/bulking agent, wherein after reconstitution with water affords a water-containing emulsion with identical particle size distribution as the original water-containing emulsion.

2. The composition of claim 1 which further comprises hydrophilic emulsifiers and acetylated monoglycerides.

3. The composition of claim 2 wherein the hydrophilic emulsifier comprises ethoxylated triglycerides or polyoxyethylene hydroxy fatty acid esters and the acetylated monoglycerides contain unsaturated double bonds.

4. The composition of claim 2 wherein the hydrophilic emulsifier is glycerol polyethylene glycol ricinoleate or polyoxyethylene 660 12-hydroxystearate and the acetylated monoglycerides are diacetylated monoglycerides or a mixture of diacetylated and partially acetylated monoglycerides.

5. The composition of claim 2 comprising about 2 to 40 wt % acetylated monoglycerides.

6. The composition of claim 5 wherein the acetylated monoglycerides comprise about 20 wt % of partially acetylated monoglycerides.

7. The composition of claim 2 wherein the hydrophilic emulsifiers and the acetylated monoglycerides are present in a weight ratio of about 1:10 to 2:1.

8. The composition of claim 7 wherein said weight ratio is about 2:3.

9. The composition of claim 1 wherein the active substance is a prostaglandin.

10. The composition of claim 9 wherein said prostaglandin is $PGE_1$.

11. The composition of claim 1 wherein said cryoprotection/bulking agent comprises physiological tolerated mono-, di- or oligosaccharides.

12. The composition of claim 11 wherein said saccharides are selected from lactose, sorbitol, and mannitol.

13. The composition of claim 1 which further comprises an antioxidant.

14. The composition of claim 13 wherein said antioxidant is $\alpha$-, $\beta$-, $\Gamma$-, or $\delta$-tocopherol or a physiologically tolerated buffer salt or mixture thereof.

15. The composition of claim 14 wherein the physiologically tolerated salt is a phosphate, succinate or acetate.

16. The composition of claim 14 wherein the antioxidant is $\alpha$-tocopherol.

17. The composition of claim 1 wherein said composition, after reconstitution with water, has an average particle diameter of about 0.1 μm to about 3 μm.

18. The composition of claim 17 wherein the average particle diameter is about 0.2 μm to about 1.0 μm.

* * * * *